(12) United States Patent
Dharmadhikari et al.

(10) Patent No.: US 7,105,178 B2
(45) Date of Patent: Sep. 12, 2006

(54) CARDIOTONIC COMPOSITION

(75) Inventors: Nitin Bhalachandra Dharmadhikari, Maharashtra (IN); Vaishali Vijay Dhavse, Maharashtra (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 10/415,098

(22) PCT Filed: Dec. 7, 2001

(86) PCT No.: PCT/IN01/00216

§ 371 (c)(1),
(2), (4) Date: Apr. 30, 2003

(87) PCT Pub. No.: WO03/007968

PCT Pub. Date: Jan. 30, 2003

(65) Prior Publication Data

US 2004/0048809 A1    Mar. 11, 2004

(30) Foreign Application Priority Data

Jul. 17, 2001    (IN)    .................. 681/MUM/2001

(51) Int. Cl.
*A61K 9/20*    (2006.01)
*A61K 31/70*    (2006.01)
(52) U.S. Cl. ............................. 424/464; 514/25; 514/61
(58) Field of Classification Search .................. 514/25, 514/61; 424/464
See application file for complete search history.

(56) References Cited

FOREIGN PATENT DOCUMENTS

| | | |
|---|---|---|
| EP | 1 027 887 A2 | 8/2000 |
| EP | 1 120 109 A2 | 8/2001 |
| EP | 1 125 576 A1 | 8/2001 |
| WO | WO 00/06126 | 2/2000 |
| WO | WO 00/18374 | 4/2000 |
| WO | WO 00/72827 A2 | 12/2000 |

*Primary Examiner*—Elli Peselev
(74) *Attorney, Agent, or Firm*—Westerman, Hattori, Daniels & Adrian LLP

(57) ABSTRACT

A cardiotonic composition includes micronized digoxin, hydrophilic polymer(s) and optionally pharmaceutically acceptable excipient(s) in the form of a tablet that releases not more than 50% digoxin in 5 minutes and at least 85% digoxin in 60 minutes.

10 Claims, No Drawings

CARDIOTONIC COMPOSITION

FIELD OF INVENTION

The present invention relates to a cardiotonic composition. More specifically, the present invention relates to a cardiotonic composition that releases digoxin reproducibly at a specified rate over a duration of 1 hour.

BACKGROUND OF THE INVENTION

Digoxin, one of the cardiac (or digitalis) glycosides, is known for use in the treatment of congestive heart failure. When administered at the proper therapeutic dosage level, digoxin exerts a direct cardiotonic effect on the myocardium to increase the force of contraction and improve cardiac tone. It has a narrow therapeutic index, i.e. the dose producing the toxic or other undesirable side effects is not much greater than the therapeutically effective dose. Several side effects encountered in the treatment with cardiac glycosides are related to a peak in plasma concentration often occurring a few hours after administration of a dose. Very rapid initial rate of release results in higher peak plasma levels and therefore more side effects. On the other hand, if digoxin is released too slowly from tablets into gastrointestinal fluids then incomplete absorption occurs. The United States Pharmacopoeia [USP XXIV & NF XIX (The United States Pharmacopoeia Convention, Inc., Rockville, Md. 1999)] sets a specification for digoxin tablets requiring that at least 85% digoxin be released in 60 minutes.

German Patent DE 1467788 discloses compositions that contain digoxin in solution, sodium alginate and polyacryahnide for gradual and controlled release of digoxin. The patent relates to a liquid composition and does not teach or disclose the preparation of a tablet dosage form providing the desired release profile of the present invention.

Prior art compositions either relate to improving the solubility or dissolution rate of digoxin to enhance its bioavailability or relates to enteric coated compositions that do not release digoxin in acidic gastric fluids or relate to controlled release of digoxin over much longer periods than stipulated herein in the present invention. Whereas very rapid initial rate of release results in higher plasma level and more side effects, prior art does not discuss or disclose a composition that releases not more than 50% digoxin at 5 minutes when tested in vitro in United States Pharmacopoeia Type I Dissolution apparatus using 500 ml of 0.1N HCl at 120 rpm for 60 minutes at 37° C. The commercial tablets marketed under the name Lanoxin® releases more than 50% digoxin at 5 minutes when tested under these conditions.

OBJECT OF THE INVENTION

It is the object of the instant invention to provide a cardiotonic composition in the form of a tablet that releases not more than 50% digoxin in 5 minutes and at least 85% of digoxin in 60 minutes when tested in vitro in United States Pharmacopoeia Type I Dissolution apparatus using 500 ml of 0.1N HCl at 120 rpm for 60 minutes at 37° C.

SUMMARY OF THE INVENTION

The present invention provides a cardiotonic composition comprising micronized digoxin, hydrophilic polymer(s) and optionally pharmaceutically acceptable excipient(s) in the form of a tablet that releases not more than 50% digoxin in 5 minutes and at least 85% of digoxin in 60 minutes when tested in vitro in United States Pharmacopoeia Type I Dissolution apparatus using 500 ml of 0.1N HCl at 120 rpm for 60 minutes at 37° C.

Preferably, the cardiotonic composition of the present invention releases at least 50% of digoxin in 15 minutes when tested as described above.

DETAILED DESCRIPTION OF THE INVENTION

The cardiotonic composition of the present invention is in the form of a matrix formulation. The matrix formulation comprises micronized digoxin and hydrophilic polymer and optionally other pharmaceutically acceptable excipients. Preferably, the digoxin used in the present invention is in the micronized form wherein at least 50% of the particles are less than 15 microns; at least 90% of the particles are less than 25 microns and at least 99% of the particles are less than 50 microns.

The digoxin is used in an amount sufficient to deliver a therapeutically effective amount of the drug over the delivery period. Generally the amount may be between 100 micrograms to 500 micrograms, more particularly it is 250 microgram per unit dosage form.

According to the present invention, the release rate of digoxin is controlled with the aid of hydrophilic polymer(s). Examples of hydrophilic polymers that may be used in the present invention include but are not limited to:

cellulose ethers such as methylcellulose (MC), ethylcellulose (EC), hydroxyethylcellulose (HEC), hydroxypropyl cellulose (BPC), hydroxypropyl methylcellulose (HPMC), hydroxypropyl ethylcellulose (HPEC), carboxymethyl cellulose (CMC), crosslinked carboxymethyl cellulose (croscarmellose) and its alkali salts, ethylhydroxyethylcellulose (EHEC), hydroxyethyl methylcellulose (HEMC), hydrophobically modified hydroxyethyl cellulose (AZTEC), hydrophobically modified ethylhydroxyethylcellulose HEC), carboxymethyl hydroxyethylcellulose (CMHEC), carboxymethyl hydrophobically modified hydroxyethyl cellulose (CMHMHEC), and the like;

alkylene oxide homopolymers such as polypropylene oxide, preferably ethylene oxide homopolymers gums of plant, animal, mineral or synthetic origin such as (i) agar, alginates, cartageenan, furcellaran derived from marine plants, (ii) guar gum, gum arabic, gum tragacanth, karaya gum, locust bean gum, pectin derived from terrestrial plants, (iii) microbial polysaccharides such as dextran, gellan gum, rhamsan gum, welan gum, xanthan gum, and (iv) synthetic or semi-synthetic gums such as propylene glycol alginate, hydroxypropyl guar and the like; and an acrylic acid polymer such as cross-linked polymer available under the tradename Carbopol® or homopolymers and copolymers of acrylate or methacrylate monomers for example polymethacrylates marketed under the brand names of Eudragit®.

More preferably, the hydrophilic polymer(s) used in the present invention is a cellulose ether, preferably hydroxypropyl methylcellulose. Preferably, the hydroxypropyl methylcellulose used in the present invention has a methoxy % ranging from about 18 to 30% and hydroxypropyl % ranging from about 8 to about 25%. More preferably, the hydroxypropyl methylcellulose selected is such that its methoxy content ranges from about 20 to 30% and hydroxypropyl content ranges from about 5 to 10%. Further more preferably, the hydroxypropyl methylcellulose selected has methoxy content of about 29% and hydroxypropyl content of about 8.5%. Most preferably, the hydroxypropyl methylcellulose is such that it exhibits a viscosity of about 15 centipoise. (Viscosity value for 2% w/v aqueous solution measured at 20° C.). The amount of hydroxypropyl methylcellulose used in the present invention may range from 5% w/w to about 7% w/w of the total weight of the dosage form.

In one of the preferred embodiments, purified water is used as the granulating agent.

Further, additional pharmaceutical excipients may be present in the core. Examples of other additional excipients include those excipients which are used in tableting, during the preparation of granules, e.g. diluents, lubricants, glidants, dispersants, colorants and the like. One or more pharmaceutically inert diluent(s) used in the present invention is/are selected from a group consisting of calcium phosphate dibasic anhydrous, calcium phosphate dibasic dihydrate, calcium phosphate tribasic, carboxymethylcellulose calcium, cellulose microcrystalline, pregelatinized starch, silicified microcrystalline cellulose, sorbitol, starch, dipotassium hydrogen orthophosphate, dipotassium phosphate, dextrates, dextrin, dextrose, lactose monohydrate, magnesium carbonate, magnesium carbonate, maltitol, maltodextrin, maltose, cellulose and the like.

Preferably, the diluent(s) used in the present invention is/are selected from a group consisting of dextrates, dextrin, dextrose, lactose monohydrate, magnesium carbonate, magnesium carbonate, maltitol, maltodextrin, maltose, pregelatinized starch, cellulose, sorbitol, starch. Still preferably, the diluent(s) selected is lactose monohydrate.

The lubricants used in the present invention are typically present in an amount ranging from about 0.1% to about 2% by weight of the dosage form, preferably up to about 1.0%, more preferably about 0.75% to about 1.0% by weight of the dosage form. Most preferably, the composition of the present invention comprises of a magnesium stearate as a lubricant in an amount ranging from about 0.75 to 1.0% w/w of the total weight of the dosage form. Preferably, the magnesium stearate is used in the concentration of about 0.5% of the total weight of the dosage form.

According to the present invention the cardiotonic composition comprises of micronized digoxin, hydrophilic polymer(s) and optionally pharmaceutically acceptable excipient (s) in the form of a tablet that releases not more than 50% digoxin in 5 minutes and at least 85% digoxin in 60 minutes when tested in vitro in United States Pharmacopoeia Type I Dissolution apparatus using 500 ml of 0.1N HCl at 120 rpm for 60 minutes at 37° C.

More preferably the cardiotonic composition prepared according to the present invention releases at least 50% digoxin in 15 minutes when tested as described above.

The cardiotonic composition of the present invention when orally administered to human volunteers at a dose of 500 µg provides a peak plasma level in the range of 1.8 to 2.8 ng/ml.

The oral drug delivery of the present invention is prepared by known methods, e.g. by mixing, granulation, compression, coating, etc. The mixture may be dry granulated, wet granulated or can be directly compressed. In the case of dry granulation, the dry mixture of micronized digoxin, hydrophilic polymer(s) and the excipients, is passed through a chilsonator to obtain slugs of the material, which are then passed through suitable sieves to obtain granules. In wet granulation, water is preferred as the granulating agent. The entire mix is then granulated and the granules after lubrication are eventually compressed on a rotary compression machine using standard concave beveled edge punches. In case of direct compression, the components of the system are mixed thoroughly and directly compressed on a rotary compression machine.

The Examples that follow do not limit the scope of the invention and are presented as illustrations.

EXAMPLE 1

This example describes an embodiment of the preparation of a cardiotonic composition of the present invention comprising digoxin. The tablets were prepared according to the formula given in Table 1.

TABLE 1

| Sr. No | Ingredients | Mg/Tablet | % w/w |
|---|---|---|---|
| 1 | Digoxin micronized | 0.25 | 0.2083 |
| 2 | Lactose monohydrate | 111.65 | 93.0416 |
| 3 | Hydroxy Propyl methyl cellulose 15 cps | 7.5 | 6.25 |
| 4 | Purified water | q.s | q.s |
| 5 | Magnesium stearate | 0.6 | 0.5 |
| | Total | 120.0 | 100 |

The particle size distribution data of the micronized digoxin is given in Table 2. As evidenced from the data, the particle size distribution can therefore be specified as at least 50% of the particles are less than 15 microns, at least 90% of the particles are less than 25 microns and at least 99% of the particles are less than 50 microns.

TABLE 2

| Particle size in micrometers | % Distribution |
|---|---|
| 0–10 | 84% |
| 10–25 | 10% |
| 25–50 | 3% |
| >50 | <2% |

Digoxin (micronized) was mixed with small quantity of lactose monohydrate and passed through 40 Mesh sieve. This blend was charged in mixer, sandwiching between lactose and Hydroxy propyl methylcellulose and mixed for 5 minutes. The powder mixture was granulated with purified water till the wet mass attained optimum consistency. The granules were dried at about 45–55° C. in the tray drier to a Loss on Drying of 1–3%. The dry granules were sifted through 20 mesh sieve. The oversize granules were milled through multimill fitted with 2 mm screen at slow speed and again passed through 20 mesh sieve. The milled granules were blended with magnesium stearate in a double cone blender for 5 minutes. The granules were compressed on 7.0 mm round, standard concave punches at compression weight of 120 mg.

EXAMPLE 2

COMPARATIVE EXAMPLE

The composition was prepared according to process described in the example 1. The tablets were prepared according to the formula given in Table 3.

TABLE 3

| Sr. No | Ingredients | Mg/Tablet | % w/w |
|---|---|---|---|
| 1 | Digoxin micronized | 0.25 | 0.2083 |
| 2 | Lactose monohydrate | 108.15 | 90.125 |
| 3 | Pregelatinized Starch | 5.0 | 4.167 |
| 4 | Purified water | q.s | q.s |
| 5 | Magnesium stearate | 0.6 | 0.5 |
|   | Total | 120.0 | 100 |

EXAMPLE 3

COMPARATIVE EXAMPLE

The composition was prepared according to the process described in Example 1 using the formula as given in Table 4.

TABLE 4

| Sr. No | Ingredients | Mg/Tablet | % w/w |
|---|---|---|---|
| 1 | Digoxin microcrystalline | 0.25 | 0.2083 |
| 2 | Lactose monohydrate | 108.15 | 90.125 |
| 3 | Pregelatinized Starch | 5.0 | 4.167 |
| 4 | Purified water | q.s | q.s |
| 5 | Magnesium stearate | 0.6 | 0.5 |
|   | Total | 120.0 | 100 |

EXAMPLE 4

The dissolution profile of the tablets of Example 1, 2, 3 and commercial tablets marketed under the brand name of Lanoxin® were tested in vitro in USP type I dissolution apparatus at 120 rpm in 500 ml of 0.1 N HCL at 37±0.5° C. The drug delivery characteristics of the tablets are recorded in Table 5 below.

TABLE 5

| Time in minutes | % release of digoxin ||||
|---|---|---|---|---|
|  | Example 1 | Example 2 | Example 3 | Commercial Tablets |
| 5 | 36 | — | — | 67 |
| 15 | 80 | 98 | 58 | 77 |
| 30 | — | 99 | 63 | — |
| 60 | 94 | 102 | 64 | 88 |

The dissolution profile of composition of Example 1 of the present invention indicated a controlled release of digoxin over a period of 60 minutes. The composition according to Example 2 released digoxin rapidly within 15 minutes. The bioavailability data for Example 2 as described in Table 6 also indicated a higher peak plasma levels which may lead to untoward side effects. The dissolution profile of Example 3 indicated an undesirable, incomplete release profile. This effect was attributed to the microcrystalline nature of digoxin. The commercial tablets marketed under the name Lanoxin® releases more than 50% digoxin at 5 minutes as indicated by its release profile.

EXAMPLE 5

The bioavailability of digoxin from compositions prepared according to process described in Example 1 and Example 2 were evaluated. The design of the study was a single dose, open table randomized, comparative two-way crossover study in comparison to Lanoxin® commercial digoxin Tablets by Burroughs Welcome in ten human volunteers under fasting conditions. Each subject received, in random sequence, an oral dose of two tablets of 0.25 mg digoxin with 240 ml of water at ambient temperature. A wash out period of 21 days was given in between the doses. The bioavailability parameters such as $C_{max}$, $T_{max}$ and AUC were recorded. The results are given in Table 6 and Table 7 for Example 2 and Example 1, respectively.

TABLE 6

| Parameters | Data ||
|---|---|---|
|  | Example 2 | Commercial Tablet |
| $C_{max}$ (ng/ml) | 3.225 | 2.379 |
| $T_{max}$ | 1.2 | 0.95 |
| In AUC 0–48 ng.hr/ml | 26.463 | 25.84 |
| Number of volunteers | 10 ||

TABLE 7

| Parameters | Data ||
|---|---|---|
|  | Example 1 | Commercial Tablet |
| $C_{max}$ (ng/ml) | 2.27 | 2.65 |
| $T_{max}$ | 1.45 | 1.03 |
| In AUC 0–48 ng.hr/ml | 23.19 | 24.90 |
| Number of volunteers | 10 ||

The in vitro dissolution profile of composition according to Example 2 as given in Table 5 indicates a rapid release of 98% of digoxin in 15 minutes. Moreover, the bioavailability data as described in Table 6 shows higher peak plasma which may lead to untoward side effects.

The in vitro dissolution profile of the composition according to Example 1 as given in Table 5 indicates a controlled release of digoxin over a duration of 60 minutes. The bioavailability study as described in Table 7 indicates a desirable peak plasma level of 2.27 ng/ml as compared to the Commercial Tablets justifying the object of the present invention.

The invention claimed is:

1. A cardiotonic composition comprising micronized digoxin wherein the micronized digoxin is such that at least 50% of the particles are less than 15 microns, at least 90% of the particles are less than 25 microns, at least 99% of the particles are less than 50 microns, and about 13% of the particles are from 10 to 50 microns, hydrophilic polymer(s) and optionally pharmaceutically acceptable excipient(s) in the form of a tablet that releases not more than 50% digoxin in 5 minutes and at least 85% digoxin in 60 minutes when tested in vitro in United States Pharmacopoeia Type I Dissolution apparatus using 500 ml of 0.1N HCl at rpm of 120 for 60 minutes at 37° C.

2. A cardiotonic composition as claimed in claim 1 wherein the tablets release at least 50% of digoxin in 15 minutes.

3. A cardiotonic composition as claimed in claim 1 wherein the amount of digoxin per unit dosage form is 250 micrograms.

4. A cardiotonic composition as claimed in claim 1 wherein the amount of digoxin per unit dosage form is 125 micrograms.

5. A cardiotonic composition as claimed in claim 1 wherein the hydrophilic polymer is a cellulose ether polymer.

6. A cardiotonic composition as claimed in claim 5 wherein the cellulose ether is a hydroxypropyl methylcellulose having a methoxy content of 29% and a hydroxypropyl content of 8.5%.

7. A cardiotonic composition as claimed in claim 1 wherein the cardiotonic composition comprises of about 0.228% w/w of micronized digoxin, about 7% w/w of hydroxypropyl methylcellulose, about 0.5% w/w of magnesium stearate and about 90% of lactose monohydrate.

8. A cardiotonic composition as claimed in claim 3 wherein the cardiotonic composition when orally administered to human volunteers provides peak plasma level in the range of 1.8 to 2.8 ng/ml.

9. A cardiotonic composition as claimed in claim 1 wherein the micronized digoxin having particle size greater than 1 micron and less than 50 microns has been prepared by milling and sifting.

10. A cardiotonic composition as claimed in claim 1 wherein about 10% of the particles are from 10 to 25 microns.

* * * * *